(12) United States Patent
Weir

(10) Patent No.: US 8,216,214 B2
(45) Date of Patent: Jul. 10, 2012

(54) POWER MODULATION OF A SCANNING BEAM FOR IMAGING, THERAPY, AND/OR DIAGNOSIS

(75) Inventor: Michael P. Weir, Blanchester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1487 days.

(21) Appl. No.: 11/716,911

(22) Filed: Mar. 12, 2007

(65) Prior Publication Data

US 2008/0226034 A1 Sep. 18, 2008

(51) Int. Cl.
- *A61B 18/18* (2006.01)
- *A61B 6/00* (2006.01)
- *A61N 5/01* (2006.01)

(52) U.S. Cl. ............. 606/9; 600/476; 606/2; 607/88

(58) Field of Classification Search .......... 128/898; 606/9; 607/88–94; 600/476

See application file for complete search history.

(56) References Cited

U.S. PATENT DOCUMENTS

| | | |
|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |

(Continued)

FOREIGN PATENT DOCUMENTS

DE 3837248 5/1990

(Continued)

OTHER PUBLICATIONS

Invitation to Pay Additional Fees with Partial International Search Report, PCT/US2008/074275 (Jan. 16, 2009).

(Continued)

*Primary Examiner* — Henry M Johnson, III
(74) *Attorney, Agent, or Firm* — Thompson Hine L.L.P.

(57) ABSTRACT

An assembly comprising a radiation source to generate a beam of radiation, a modulator for modulating the power of the beam of radiation as a function of the position of the beam within a field-of-view to maintain the beam's power within a desired exposure level as the beam scans the field-of-view, and a reflector oscillating in a sinusoidal manner to direct the beam of radiation onto a field-of-view.

16 Claims, 10 Drawing Sheets

U.S. PATENT DOCUMENTS

| | | | |
|---|---|---|---|
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |

| | | | | | | |
|---|---|---|---|---|---|---|
| 6,470,124 B1 | 10/2002 | Le Gargasson et al. | 7,013,730 B2 | 3/2006 | Malametz | |
| 6,477,403 B1 | 11/2002 | Eguchi et al. | 7,015,956 B2 | 3/2006 | Luo et al. | |
| 6,478,809 B1 | 11/2002 | Brotz | 7,018,401 B1 | 3/2006 | Hyodoh et al. | |
| 6,485,413 B1 | 11/2002 | Boppart et al. | 7,023,402 B2 | 4/2006 | Lewis et al. | |
| 6,492,962 B2 | 12/2002 | Melville et al. | 7,025,777 B2 | 4/2006 | Moore | |
| 6,494,578 B1 | 12/2002 | Plummer et al. | 7,033,348 B2 | 4/2006 | Alfano et al. | |
| 6,503,196 B1 | 1/2003 | Kehr et al. | 7,035,777 B2 | 4/2006 | Araki et al. | |
| 6,510,338 B1 | 1/2003 | Irion et al. | 7,061,450 B2 | 6/2006 | Bright et al. | |
| 6,512,622 B2 | 1/2003 | Wine et al. | 7,065,301 B2 | 6/2006 | Shastri et al. | |
| 6,513,939 B1 | 2/2003 | Fettig et al. | 7,066,879 B2 | 6/2006 | Fowler et al. | |
| 6,515,278 B2 | 2/2003 | Wine et al. | 7,071,594 B2 | 7/2006 | Yan et al. | |
| 6,515,781 B2 | 2/2003 | Lewis et al. | 7,071,931 B2 | 7/2006 | Tegreene et al. | |
| 6,520,972 B2 | 2/2003 | Peters | 7,078,378 B1 | 7/2006 | Owen et al. | |
| 6,522,444 B2 | 2/2003 | Mandella et al. | 7,083,609 B2 * | 8/2006 | Chernyak | 606/5 |
| 6,525,310 B2 | 2/2003 | Dunfield | 7,108,656 B2 | 9/2006 | Fujikawa et al. | |
| 6,527,708 B1 | 3/2003 | Nakamura et al. | 7,112,302 B2 | 9/2006 | Yoshimi et al. | |
| 6,529,770 B1 | 3/2003 | Grimblatov | 7,126,903 B2 | 10/2006 | Feenstra et al. | |
| 6,530,698 B1 | 3/2003 | Kuhara et al. | 7,189,961 B2 | 3/2007 | Johnston et al. | |
| 6,535,183 B2 | 3/2003 | Melville et al. | 7,190,329 B2 | 3/2007 | Lewis et al. | |
| 6,535,325 B2 | 3/2003 | Helsel et al. | 7,232,071 B2 | 6/2007 | Lewis et al. | |
| 6,537,211 B1 | 3/2003 | Wang et al. | 7,271,383 B2 | 9/2007 | Chee | |
| 6,538,625 B2 | 3/2003 | Tidwell et al. | 7,391,013 B2 | 6/2008 | Johnston et al. | |
| 6,545,260 B1 | 4/2003 | Katashiro et al. | 7,448,995 B2 * | 11/2008 | Wiklof et al. | 600/173 |
| 6,560,028 B2 | 5/2003 | Melville et al. | 7,580,007 B2 * | 8/2009 | Brown et al. | 345/15 |
| 6,563,105 B2 | 5/2003 | Seibel et al. | 2001/0055462 A1 | 12/2001 | Seibel | |
| 6,563,106 B1 | 5/2003 | Bowers et al. | 2002/0015724 A1 | 2/2002 | Yang et al. | |
| 6,572,606 B2 | 6/2003 | Kliewer et al. | 2002/0024495 A1 | 2/2002 | Lippert et al. | |
| 6,583,117 B2 | 6/2003 | Owen et al. | 2002/0050956 A1 | 5/2002 | Gerhard et al. | |
| 6,583,772 B1 | 6/2003 | Lewis et al. | 2002/0075284 A1 | 6/2002 | Rabb, III | |
| 6,585,642 B2 | 7/2003 | Christopher | 2002/0088925 A1 | 7/2002 | Nestorovic et al. | |
| 6,603,552 B1 | 8/2003 | Cline et al. | 2002/0115922 A1 | 8/2002 | Waner et al. | |
| 6,608,297 B2 | 8/2003 | Neukermans et al. | 2002/0141026 A1 | 10/2002 | Wiklof et al. | |
| 6,639,570 B2 | 10/2003 | Furness, III et al. | 2002/0158814 A1 | 10/2002 | Bright et al. | |
| 6,639,719 B2 | 10/2003 | Tegreene et al. | 2002/0163484 A1 | 11/2002 | Furness, III et al. | |
| 6,650,877 B1 | 11/2003 | Tarbouriech et al. | 2002/0167462 A1 | 11/2002 | Lewis et al. | |
| 6,653,621 B2 | 11/2003 | Wine et al. | 2002/0171776 A1 | 11/2002 | Tegreene et al. | |
| 6,654,158 B2 | 11/2003 | Helsel et al. | 2002/0171937 A1 | 11/2002 | Tegreene et al. | |
| 6,661,393 B2 | 12/2003 | Tegreene et al. | 2003/0016187 A1 | 1/2003 | Melville et al. | |
| 6,674,993 B1 | 1/2004 | Tarbouriech | 2003/0030753 A1 | 2/2003 | Kondo et al. | |
| 6,685,804 B1 | 2/2004 | Ikeda et al. | 2003/0032143 A1 | 2/2003 | Neff et al. | |
| 6,687,034 B2 | 2/2004 | Wine et al. | 2003/0034709 A1 | 2/2003 | Jerman | |
| 6,689,056 B1 | 2/2004 | Kilcoyne et al. | 2003/0058190 A1 | 3/2003 | Lewis et al. | |
| 6,699,170 B1 | 3/2004 | Crocker et al. | 2003/0086172 A1 | 5/2003 | Urey | |
| 6,700,552 B2 | 3/2004 | Kollin et al. | 2003/0092995 A1 | 5/2003 | Thompson | |
| 6,714,331 B2 | 3/2004 | Lewis et al. | 2003/0130562 A1 | 7/2003 | Barbato et al. | |
| 6,734,835 B2 | 5/2004 | Tidwell et al. | 2003/0142934 A1 | 7/2003 | Pan et al. | |
| 6,736,511 B2 | 5/2004 | Plummer et al. | 2003/0159447 A1 | 8/2003 | Sergio et al. | |
| 6,741,884 B1 | 5/2004 | Freeman et al. | 2003/0214460 A1 | 11/2003 | Kovacs | |
| 6,749,346 B1 | 6/2004 | Dickensheets et al. | 2003/0216729 A1 | 11/2003 | Marchitto et al. | |
| 6,755,536 B2 | 6/2004 | Tegreene et al. | 2004/0004585 A1 * | 1/2004 | Brown et al. | 345/32 |
| 6,762,867 B2 | 7/2004 | Lippert et al. | 2004/0019346 A1 * | 1/2004 | Chernyak | 606/5 |
| 6,768,588 B2 | 7/2004 | Urey | 2004/0057103 A1 | 3/2004 | Bernstein | |
| 6,771,001 B2 | 8/2004 | Mao et al. | 2004/0075624 A1 | 4/2004 | Tegreene et al. | |
| 6,782,748 B2 | 8/2004 | Weber et al. | 2004/0076390 A1 | 4/2004 | Dong Yang et al. | |
| 6,786,382 B1 | 9/2004 | Hoffman | 2004/0085261 A1 | 5/2004 | Lewis et al. | |
| 6,795,221 B1 | 9/2004 | Urey | 2004/0085617 A1 | 5/2004 | Helsel et al. | |
| 6,802,809 B2 | 10/2004 | Okada | 2004/0087844 A1 | 5/2004 | Yen | |
| 6,803,561 B2 | 10/2004 | Dunfield | 2004/0101822 A1 | 5/2004 | Wiesner et al. | |
| 6,821,245 B2 | 11/2004 | Cline et al. | 2004/0113059 A1 | 6/2004 | Kawano et al. | |
| 6,845,190 B1 | 1/2005 | Smithwick et al. | 2004/0118821 A1 | 6/2004 | Han et al. | |
| 6,856,436 B2 | 2/2005 | Brukilacchio et al. | 2004/0119004 A1 | 6/2004 | Wine et al. | |
| 6,856,712 B2 | 2/2005 | Fauver et al. | 2004/0122328 A1 | 6/2004 | Wang et al. | |
| 6,879,428 B2 | 4/2005 | Massieu | 2004/0133786 A1 | 7/2004 | Tarbouriech | |
| 6,888,552 B2 | 5/2005 | Debevec et al. | 2004/0151466 A1 | 8/2004 | Crossman-Bosworth et al. | |
| 6,894,823 B2 | 5/2005 | Taylor et al. | 2004/0155186 A1 | 8/2004 | Nestorovic et al. | |
| 6,899,675 B2 | 5/2005 | Cline et al. | 2004/0155834 A1 | 8/2004 | Wit et al. | |
| 6,902,527 B1 | 6/2005 | Doguchi et al. | 2004/0179254 A1 | 9/2004 | Lewis et al. | |
| 6,905,057 B2 | 6/2005 | Swayze et al. | 2004/0196518 A1 | 10/2004 | Wine et al. | |
| 6,939,364 B1 | 9/2005 | Soltz et al. | 2004/0199151 A1 * | 10/2004 | Neuberger | 606/9 |
| 6,957,898 B2 | 10/2005 | Yu | 2004/0223202 A1 | 11/2004 | Lippert et al. | |
| 6,967,757 B1 | 11/2005 | Allen et al. | 2004/0225222 A1 | 11/2004 | Zeng et al. | |
| 6,974,472 B2 | 12/2005 | Hong et al. | 2004/0236231 A1 | 11/2004 | McNally-Heintzelman et al. | |
| 6,975,898 B2 | 12/2005 | Seibel et al. | 2004/0240866 A1 | 12/2004 | Ramsbottom | |
| 6,976,994 B2 | 12/2005 | Ballou et al. | 2004/0252377 A1 | 12/2004 | Urey | |
| 6,978,921 B2 | 12/2005 | Shelton, IV et al. | 2004/0254474 A1 | 12/2004 | Seibel et al. | |
| 6,985,271 B2 | 1/2006 | Yazdi et al. | 2005/0010787 A1 | 1/2005 | Tarbouriech | |
| 6,991,602 B2 | 1/2006 | Nakazawa et al. | 2005/0014995 A1 | 1/2005 | Amundson et al. | |
| 7,005,195 B2 | 2/2006 | Cheng et al. | 2005/0020877 A1 | 1/2005 | Ishihara et al. | |
| 7,009,634 B2 | 3/2006 | Iddan et al. | 2005/0020926 A1 * | 1/2005 | Wiklof et al. | 600/476 |

| | | | |
|---|---|---|---|
| 2005/0023356 | A1 | 2/2005 | Wiklof et al. |
| 2005/0030305 | A1 | 2/2005 | Brown et al. |
| 2005/0038322 | A1 | 2/2005 | Banik |
| 2005/0116038 | A1 | 6/2005 | Lewis et al. |
| 2005/0162762 | A1 | 7/2005 | Novak |
| 2005/0177139 | A1* | 8/2005 | Yamazaki et al. ............... 606/9 |
| 2005/0185235 | A1* | 8/2005 | Cannon et al. ............... 359/204 |
| 2005/0187441 | A1 | 8/2005 | Kawasaki et al. |
| 2005/0187540 | A1* | 8/2005 | Mrochen et al. ............... 606/5 |
| 2005/0203343 | A1 | 9/2005 | Kang et al. |
| 2005/0240147 | A1 | 10/2005 | Makower et al. |
| 2006/0010985 | A1 | 1/2006 | Schneider |
| 2006/0084867 | A1 | 4/2006 | Tremblay et al. |
| 2006/0164330 | A1 | 7/2006 | Bright et al. |
| 2006/0183246 | A1 | 8/2006 | Wiesner et al. |
| 2006/0195014 | A1 | 8/2006 | Seibel et al. |
| 2006/0238774 | A1 | 10/2006 | Lindner et al. |
| 2006/0245971 | A1 | 11/2006 | Burns et al. |
| 2006/0284790 | A1 | 12/2006 | Tegreene et al. |
| 2007/0038119 | A1 | 2/2007 | Chen et al. |
| 2007/0046778 | A1 | 3/2007 | Ishihara et al. |
| 2007/0135770 | A1 | 6/2007 | Hunt et al. |
| 2007/0156021 | A1 | 7/2007 | Morse et al. |
| 2007/0161876 | A1 | 7/2007 | Bambot et al. |
| 2007/0162093 | A1 | 7/2007 | Porter et al. |
| 2007/0167681 | A1 | 7/2007 | Gill et al. |
| 2007/0173707 | A1 | 7/2007 | Mitra |
| 2007/0179366 | A1 | 8/2007 | Pewzner et al. |
| 2007/0197874 | A1 | 8/2007 | Ishihara |
| 2007/0197875 | A1 | 8/2007 | Osaka |
| 2007/0203413 | A1 | 8/2007 | Frangioni |
| 2007/0213588 | A1 | 9/2007 | Morishita et al. |
| 2007/0213618 | A1 | 9/2007 | Li et al. |
| 2007/0225695 | A1 | 9/2007 | Mayer et al. |
| 2007/0238930 | A1 | 10/2007 | Wiklof et al. |
| 2007/0244365 | A1 | 10/2007 | Wiklof |
| 2007/0260121 | A1 | 11/2007 | Bakos et al. |
| 2007/0260273 | A1 | 11/2007 | Cropper et al. |
| 2008/0058629 | A1 | 3/2008 | Seibel et al. |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Invitation to Pay Additional Fees with Partial International Search Report, PCT/US2008/074273 (Dec. 30, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
Ra, H. et al., "Biomedical Optics & Medical Imaging—Microtechnology enables endoscopic confocal microscopy," SPIE (http://spie.org) (2007).
Kiang, M-H et al., "Surface-Micromachined Electrostatic-Comb Driven Scanning Micromirrors for Barcode Scanners" (date of first publication unknown).
Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.com (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PlxBead™ Superior Qualities," http:www.crystalplex.com (date of first publication unknown).
"Microvision [illuminating information] Products/Overview, Corporate Overview Presentation 2006" (2006).
"Holographic Beam Combiner for Ladar, Printer, Fiber Optics, and Cancer Treatment," by Digital Optics Technologies, Inc., http://www.mdatechnology.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarzing Cube Beamsplitters," from GlobalSpec The Engineering Search Engine, http://www.globalspec.com (date of first publication unknown).
Literature entitled "Dallas Semiconductor MAXIM—Visible-Laser Driver has Digitally Controlled Power Modulation," by Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," by Johnson & Johnson, http://www.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).

PCT, International Search Report, PCT/US2008/066552 (Oct. 23, 2008).

International Search Report issued regarding International Application No. PCT/US2007/078868 (Mar. 28, 2008).

PCT, International Search Report and Written Opinion, International Application No. PCT/US2008/056596 (Jun. 23, 2008).

* cited by examiner

POWER MODULATION OF A SCANNING BEAM FOR IMAGING, THERAPY, AND/OR DIAGNOSIS

FIELD OF THE INVENTION

This invention relates to modulating the power of the beam in a scanning beam assemblies of the type that employs an oscillating reflector to control the scanning beam, as well as to scanning beam assemblies that use imaging, therapeutic, and/or diagnostic beams.

BACKGROUND OF THE INVENTION

U.S. Published Application 2005/0020926 discloses a scanned beam imager that may be used in applications in which cameras have been used in the past. In particular it can be used in medical devices such as video endoscopes, laparoscopes, etc.

The scanned beam imager disclosed in the published application has an illuminator that creates a first beam of light and a scanner that deflects the first beam of light across a field-of-view (FOV). The scanned beam of light sequentially illuminates spots in the FOV corresponding to various beam positions. While the beam illuminates the spots, the illuminating light beam is reflected, absorbed, scattered, refracted, or otherwise affected by the object or material in the FOV to produce scattered light energy. A portion of the scattered light energy travels to detectors that receive the light and produce electrical signals corresponding to the amount of light energy received, which is then converted to separate electrical signals. The electrical signals pass to a controller that builds up a digital image and transmits it for further processing, decoding, archiving, printing, display, or other treatment or use.

One example of the scanner employs a MEMS device carrying a reflector capable of deflection about two orthogonal scan axes, in which the reflector is driven in both scan axes at a frequency near their natural mechanical resonant frequencies. In another example, one axis is operated near resonance while the other is operated substantially off resonance. For completeness it is also noted that scanners are also know that employ two reflectors, one of which oscillates sinusoidally and the other of which simply scans linearly.

In a resonant scanner, the scanning reflector or reflectors oscillate such that their angular deflection in time is approximately a sinusoid, at a mechanical resonant frequency determined by the suspension stiffness and the moment of inertia of the MEMS device incorporating the reflector. Motion can be sustained with little energy and the devices can be made robust when they are operated at the mechanical resonant frequency. However, sinusoidal angular deflection is less than optimal for certain applications. The varying velocity inherent in a sinusoidal scan gives varying "exposure" at a given point in the FOV. This "exposure" is related to the power of the beam of the scanning beam imager, and its velocity, which varies over the FOV. The extremes occur in the center of the scan where the beam angular velocity is at its greatest and at the edges of the scan where the beam slows to reverse its direction across the FOV. Therefore, there is a need to modulate the power of the beam in a resonant scanning beam assembly to achieve a desired exposure at any specified part of the FOV.

SUMMARY

In accordance with this disclosure, one aspect of the present invention is an assembly that comprises a radiation source to generate a beam of radiation, a modulator for modulating the power of the beam of radiation as a function of the position of the beam within the field-of-view to maintain the beam's power within a desired exposure level as the beam scans the field-of-view, and a reflector oscillating in a sinusoidal manner to direct the beam of radiation onto a field-of-view.

In another aspect, the present invention is an assembly that comprises a radiation source to generate a beam of radiation that includes at least one of a therapeutic beam, and a diagnostic beam, a modulator for modulating the power of the beam of radiation as a function of the position of the beam within the field-of-view to maintain the beam's power within a desired exposure level as the beam scans the field-of-view, and a reflector oscillating in a sinusoidal manner to direct the beam of radiation onto a field-of-view, wherein the reflector is at least part of a medical instrument.

In another aspect, the present invention provides an assembly that comprises a radiation source to generate a beam of radiation, a modulator for modulating the power of the beam of radiation as a function of the velocity of the beam within a field-of-view to maintain a desired exposure level as the beam scans the field-of-view, and a reflector oscillating in a sinusoidal manner to direct the beam of radiation onto a field-of-view.

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, examples, etc. can be combined with any one or more of the other following-described embodiments, examples, etc.

Figure 1:
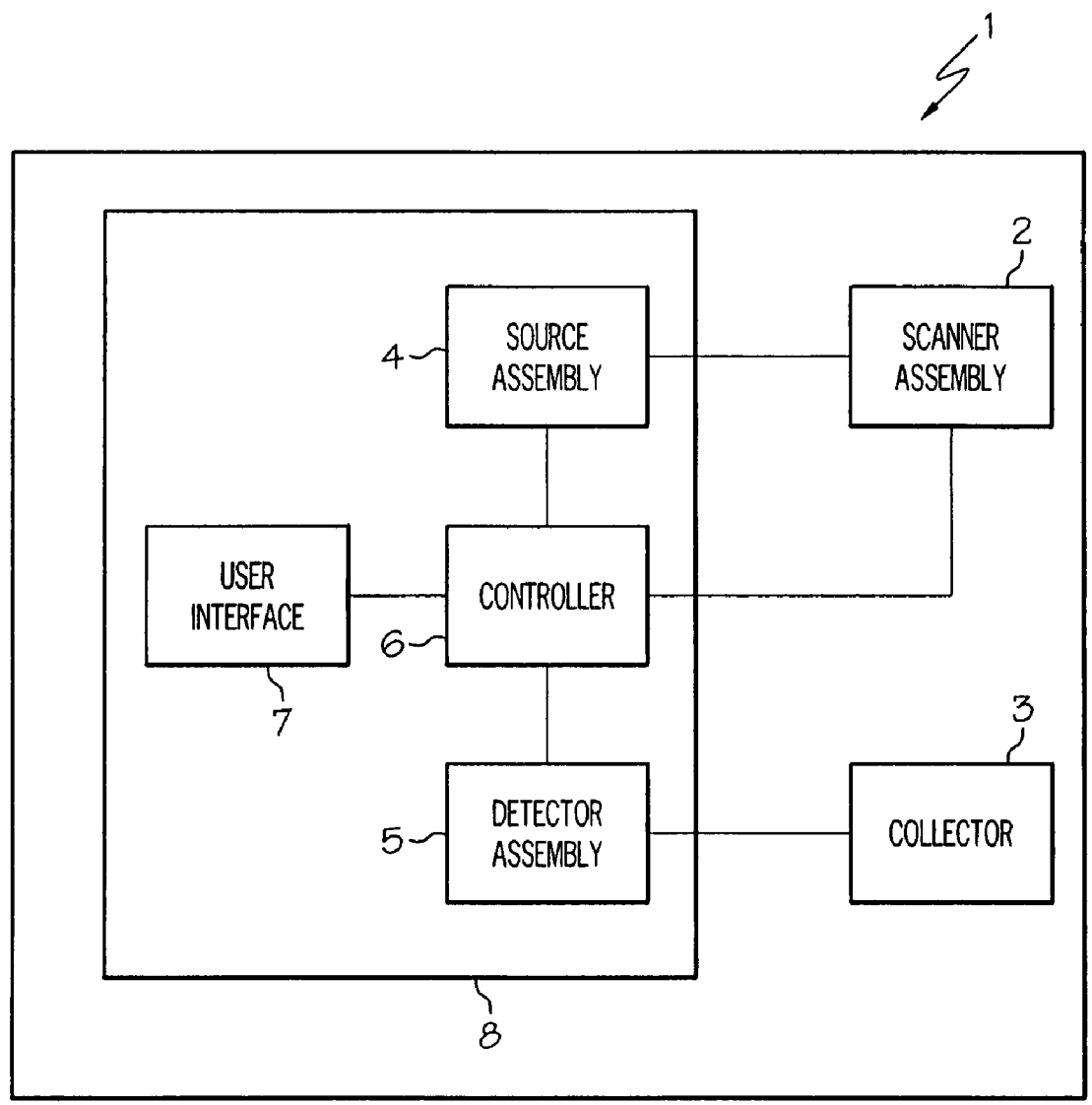
FIG. 1 is a block diagram of an embodiment of a medical device system including a scanner assembly.

Referring to FIG. 1, an embodiment of a medical device 1 includes a scanner assembly 2, a collector 3, a radiation source assembly 4, a detector assembly 5, a controller 6 and a user interface 7. The radiation source assembly 4, detector assembly 5, controller 6 and user interface 7 make up functional element 8 that is known herein as a "console." The radiation source assembly 4, as selected by the user via the user interface 7, and acting through the controller 6, generates at least two wavelengths of radiation (e.g., in the visible wavelength range and/or otherwise). This radiation is conveyed in a beam to the scanner assembly 2, which causes the beam to be swept across a tissue surface. The extent of this swept area is generally known as the "field of view" (FOV). Radiation reflected from the scene within the FOV may be intercepted by the collector 3 and passed to the detector assembly 5. The detector assembly converts the received radiation to electrical signals that are then configured by the controller to form an image on a display device in the user interface 7.

Figure 2:
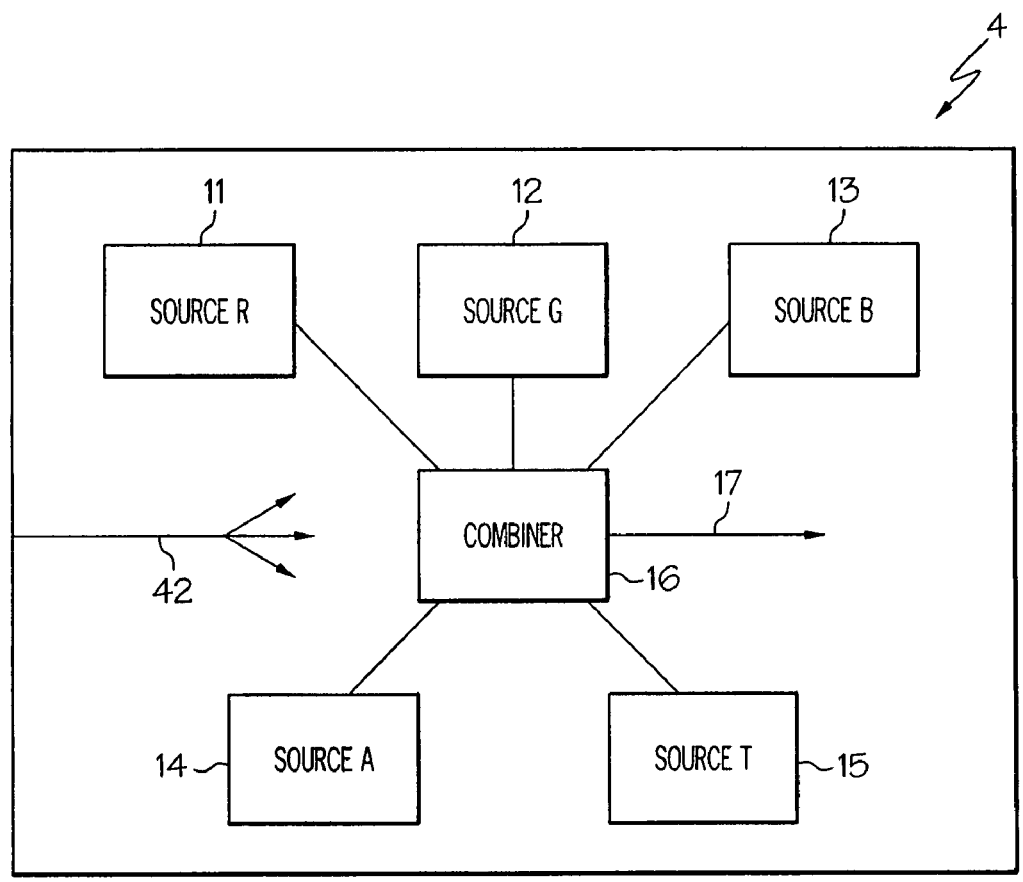
FIG. 2 is a block diagram of an embodiment of a source assembly including multiple sources for generating imaging, therapeutic and aiming beams.

FIG. 2 is a block diagram of one implementation of the source assembly 4. Source assembly 4 includes multiple sources, each capable of generating radiation at a selected wavelength. Five sources are shown here, numbered 11 thru 15. The outputs of the radiation sources 11-15 may, in some embodiments, be brought together in combiner element 16 to yield an output beam 17. Combiner 16 may also include beam-shaping optics such as one or more collimating lenses and/or apertures. The sources may be of various types such as, for instance, light emitting diodes (LEDs), lasers, thermal sources, arc sources, fluorescent sources, gas discharge sources, or others. Signals 42 may be provided by controller 6 (FIG. 1) to one or more of the sources and optionally the combiner 16. Signals 42 may optionally control wavelength, power, modulation or other beam properties.

The wavelength of radiation, for example, may be selected for imaging, therapy, or aiming. As used herein, an "imaging beam" refers to radiation selected for use in creating an image of a surface or region, a "therapeutic beam" refers to radiation selected to provide treatment of a condition such as diseased or damaged tissue, and an "aiming beam" refers to radiation selected to accentuate a portion of the FOV. Various uses and applications of such beams are disclosed in U.S. patent application Ser. No. 11/716,806, titled MEDICAL DEVICE INCLUDING SCANNED BEAM UNIT FOR IMAGING AND THERAPY and filed on the same day as the instant application, the details of which are herein incorporated by reference in its entirety. In this example, sources 11, 12 and 13 emit red, green and blue radiation; source 14 emits an aiming beam at a wavelength selected to yield a distinct contrast to the typical target material; and source 15 emits a therapeutic beam at a wavelength that is highly absorbed and moreover can be efficiently generated at high power to treat diseased or damaged tissue. In some embodiments, the aiming beam may be provided by source separate from the therapeutic beam source 15. As an alternative, an aiming beam may be provided by source 15 as a reduced power therapeutic beam. In some embodiments, the aiming beam could be a virtual beam (i.e., a region in which one or more of the imaging sources is caused to increase (or decrease) significantly to create a bright (or dark) region in the displayed image.

In some embodiments, a source (not shown) provides a diagnostic beam. A "diagnostic beam" as used herein refers to radiation selected for analysis or detection of a disease or other medical condition including, for example, to visualize the presence of (or to activate) a diagnostic marker. The diagnostic marker could be naturally occurring (e.g., auto or self fluorescence) or introduced as part of the diagnostic procedure (e.g., fluorescent dyes).

Use of an aiming beam may be preferred in some circumstances. As will be seen later, while the treatment beam may follow the same path as the imaging beam, it is not constrained to follow the same timing. An aiming beam, managed in the same way as the therapeutic beam though at lower power and in a visible wavelength, may help ensure that the treatment is applied where the user intends. Furthermore, it may be a requirement of certain industry or regulatory standards such as AAMI or IEC that where higher power lasers are employed, an aiming beam be provided.

It should be noted that while five sources are illustrated, there may be more or fewer emitters depending, for example, on the end use. In some embodiments, sources may be combined or capable of providing various types of energy. In some cases, filters may be used to filter the radiation. In some embodiments, sources 11, 12 and 13 comprise three lasers; a red diode laser, a green diode-pumped solid state (DPSS) laser, and a blue DPSS laser at approximately 635 nm, 532 nm, and 473 nm, respectively. While laser diodes may be directly modulated, DPSS lasers generally require external modulation such as an acousto-optic modulator (AOM) for instance. In the case where an external modulator is used, it is considered part of the radiation source assembly and not shown separately.

Figure 3:
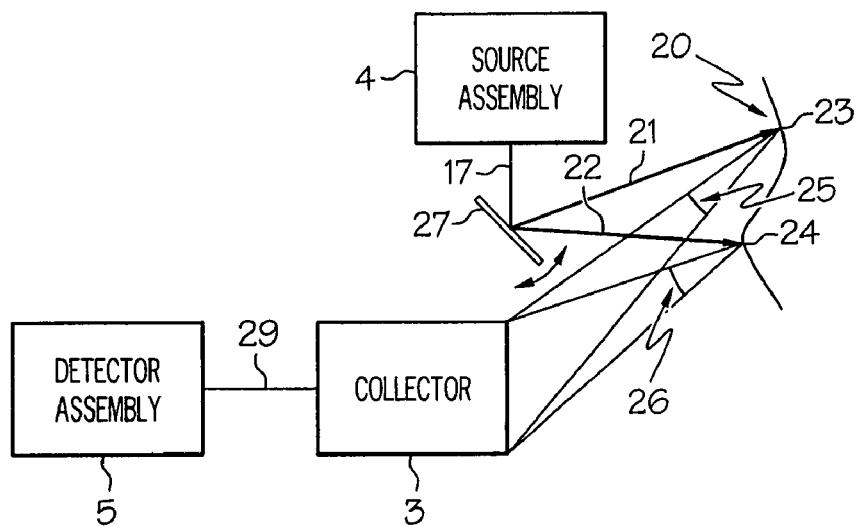
FIG. 3 is a block diagram illustrating radiation paths.

FIG. 3 illustrates the operation of a device 1 incorporating a scanner assembly 2. Reflector 27 receives a beam of radiation 17 from source assembly 4 and directs the beam onto the surface 20, for example, for one or more of imaging, therapy, or aiming purposes. At one point in time, the beam deflected by the reflector 27 is in direction shown as 21, and impinges upon the surface to illuminate a point 23. Reflector 27 oscillates in at least one axis (two axes in some embodiments), as indicated by the nearby arrowed arc, so that at some other point in time the deflected beam is in the direction indicated as 22 where, it illuminates point 24. Radiation is, in general, reflected, absorbed, scattered, refracted or otherwise affected by the properties of the surface. Radiation may leave the surface in many directions. The collector 3, however, may only capture that fraction of radiation which falls into the area subtended by its aperture. Regions 25 and 26 show the reflected radiation that is captured by the collector 3 when the beam is illuminating points 23 and 24 respectively. Directions 21 and 22 are not intended to represent any special part of the scan as the beam may be scanned using reflector 27 beyond them, and scans all points between them as well. Furthermore, a simplified two-dimensional view is represented by FIG. 3, and in general reflector 27 and collector 3 are adapted to illuminate and capture from surfaces occupying space in three dimensions.

Some embodiments use a micro-electromechanical (MEMS) scanner reflector to direct the imaging, aiming and therapeutic beams onto the surface. MEMS scanner reflectors are described in, for example, U.S. Pat. No. 6,140,979, entitled SCANNED DISPLAY WITH PINCH, TIMING, AND DISTORTION CORRECTION; U.S. Pat. No. 6,245, 590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331, 909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433, 907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled SCANNED IMAGING APPARATUS WITH SWITCHED FEEDS; U.S. Pat. No. 6,525,310, entitled FREQUENCY TUNABLE RESONANT SCANNER; and U.S. patent application Ser. No. 10/873,540, entitled SCANNING ENDOSCOPE; all of which are hereby incorporated by reference in their entirety as if fully set forth herein.

Figure 4:
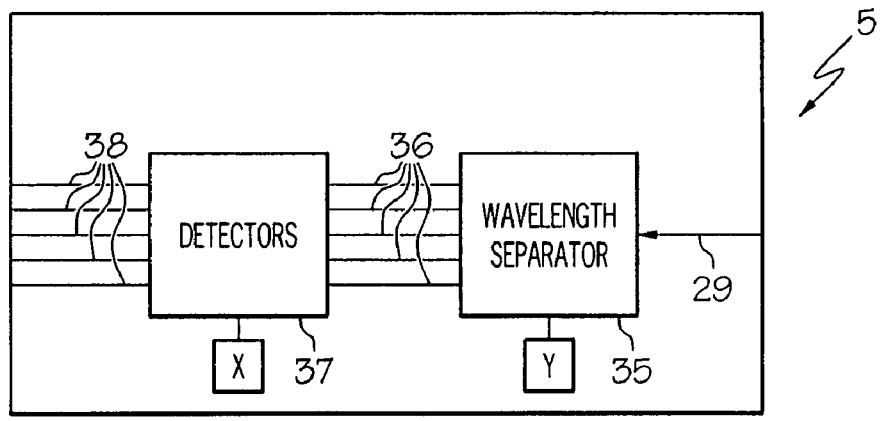
FIG. 4 is a block diagram of an embodiment of a detector assembly.

FIG. 4 is a block diagram of the exemplary detector assembly 5. Radiation 29 that is intercepted by the collector 3 is passed to the detector assembly 5. This radiation includes energy at several wavelengths, corresponding to those emitted by the source assembly 4, and possibly also including other wavelengths as may result from nonlinear processes (such as fluorescence). In some embodiments, wavelength separator 35 separates the incoming radiation 29 into pathways 36. Such separation may be performed by filters, gratings, or other devices. In an alternate configuration, wavelength separation may be incorporated in the collector 3, and separated wavelengths brought to the detectors 37, each in its own fiber or fiber bundle. Each separated wavelength of radiation is then sent to detectors 37 in the detector assembly 5. Such detectors may be physically separate, or parts of a common detector such as a CCD or CMOS device. Multiple detectors 37 may be incorporated for each wavelength. The detectors output electrical signals 38 corresponding the power, amplitude, or other characteristic of each wavelength of radiation detected. The signals can be used by a controller 6 (FIG. 6) to generate a digital image, e.g., for processing, decoding, archiving, printing, display, etc.

In some embodiments, X represents an input to the detectors 37 capable of modifying the transfer function from radiation to electric signals. Exemplary modifications may include adjustment of gain or offset or both. Y may represent an input to the wavelength separator 35 capable of modifying the transfer function therethrough. The modifying elements X and Y may be disposed to operate on the input to the respective detectors 37 and wavelength separator 35, acting on all or a subset of wavelengths received, at the outputs of the respective detectors 37 and wavelength separator 35 or at both inputs and outputs.

Figure 5:
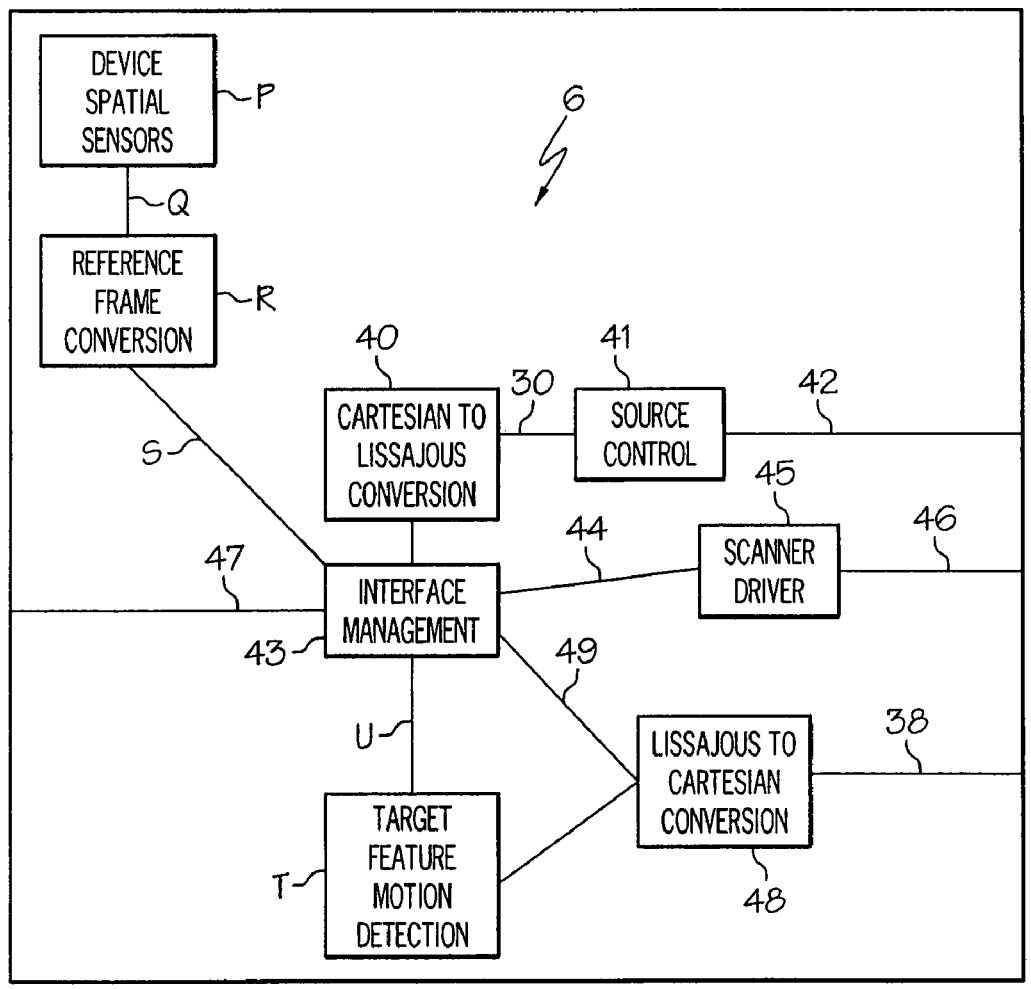
FIG. 5 is a block diagram of an embodiment of a controller for a medical device including a scanner assembly.

FIG. 5 is a block diagram of the exemplary controller 6. An interface management component 43, among other tasks, accepts operating mode commands from the user, illustrated as part of path 47. Such commands may include imaging and treatment modes, FOV and/or aspect ratio of the image, image storage, etc. Specifications related to the FOV and aspect ratio result in parameters sent via path 44 to a scanner driver 45, which generates requisite drive signals 46 to the reflector 27 (FIG. 3). The user may also specify treatment parameters, such as the location, shape and size of a region to be treated, the wavelength to be used, and duration of exposure. These result in parameters being sent to a coordinate converter 40, which converts the specifications into selection and modulation commands 30 to a source control block 41. This source control and modulation block 41 drives the source assembly 4 to provide the requisite radiation outputs 42. Signals 38 from the detector assembly 5 are converted from their scan coordinate system to a Cartesian form 49 at block 48 for display and sent to the interface management block 43 for user viewing.

In some embodiments, motion sensing is incorporated within the system via target feature motion detection, element T. For example, element P may include a number of sensors attached or connected to the scanner assembly 2. The sensors may sense location, orientation or both. The sensors may be, for example, accelerometers, magnetometers, rate gyros, electromagnetic position sensors, etc. Element Q represents the location and orientation signals generated by the sensors and element R represents a mathematic operation capable of converting the signals Q into a stationary reference frame. Element S represents output of element R which is used to modify the relationship of a displayed image to the scanned data 49 to compensate for sensed movement.

Element R operates on the scanned data 49 to detect the relative movement and provides signals U indicating magnitude and direction of the movement. This image tracking functionality may provide reliable treatment of the body which might be moving due to, for example, respiration, circulation or other biological activity.

Figure 6:
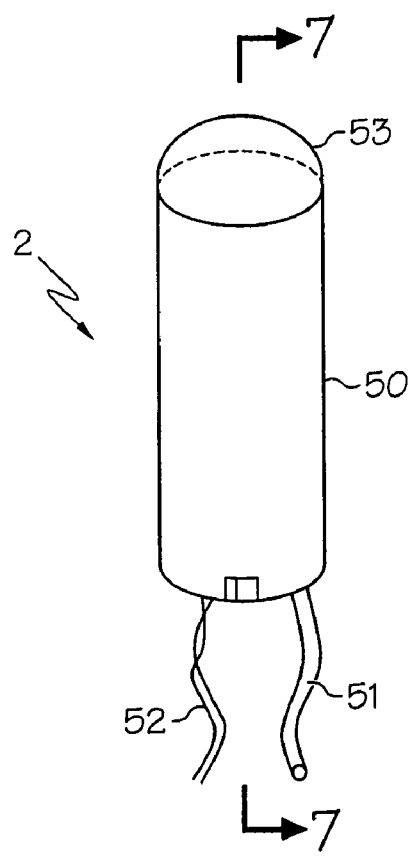
FIG. 6 is a perspective view of an embodiment of a scanner assembly.

FIG. 6 is an external view of one embodiment of the scanner assembly 2. Scanner assembly 2 includes a housing 50 that encloses the reflector 27 and other components. A source fiber 51 is used to deliver energy from the source assembly 4 to the scanner assembly 2. Source fiber 51 may be a single mode optical fiber. In some embodiments, one or more fibers may be used to deliver imaging beams and one or more other fibers may be used to deliver a therapeutic beam (e.g., therapeutic beams having longer wavelengths, e.g., greater than 1700 nm and/or higher power). In certain embodiments, a different type of fiber, such as a holey fiber, may be used to transmit energy from the source assembly 4. In some embodiments, the same optical fiber 51 is used to deliver both the imaging beams and the therapeutic beams to the reflector, the optical fiber defining a common path for both types of beams.

Electrical wires 52 convey drive signals for the reflector 27 and other signals (position feedback, temperature, etc.) to and from the scanner driver 45 (FIG. 5). Wires 52 may also provide control and feedback connections for controlling focus characteristics of the beam shaping optic 56. The distal end of the scanner assembly 2 is fitted with an optical element 53 which allows the scanned beam to pass out and illuminate the scene. This element 53 is generally referred to and illustrated as a dome; however, its curvature, contour, and surface treatments may depend on the application and optical properties required. In some embodiments, dome 53 provides a hermetic seal with the housing 50 to protect the internal elements from the environment.

Figure 7:
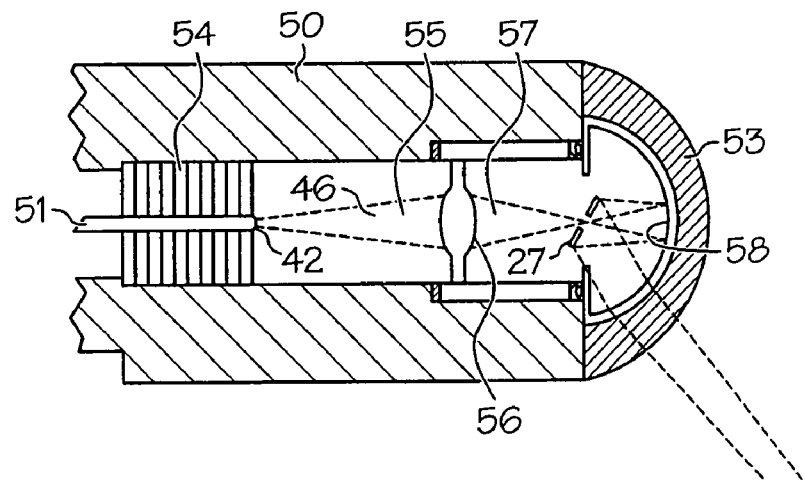
FIG. 7 is a side, section view of the scanner assembly of FIG. 6 along line 7-7.

FIG. 7 shows internal components of an embodiment of the scanner assembly 2. Source fiber 51 is affixed to the housing 50 using a ferrule 54. The end of the source fiber 51 may be polished to create a beam 55 of known divergence. The beam 55 is shaped by a beam shaping optic or lens 56 to create a beam shape appropriate for transmission through the system. After shaping, shaped beam 57 is fed through an aperture in the center of reflector 27, then reflected off a first reflecting surface 58. First reflecting surface 58 may have a beam shaping function. Beam 57 is then directed onto reflector 27 and then out of the scanner assembly 2, the details of which (in the case of an imaging beam) are described in U.S. patent application Ser. No. 10/873,540, entitled SCANNING ENDOSCOPE, the details of which are hereby incorporated by reference as if fully set forth herein. Any suitable materials can be used to form the reflector 27. In some embodiments, the reflective surface of the reflector 27 may be formed of gold or other suitable material for directing each of the beams including relative high energy therapeutic radiation. In other embodiments, a multilayer dielectric configuration may be used in forming reflector 27. In one embodiment, collecting fibers 63 may be included within housing 50.

Figure 8:
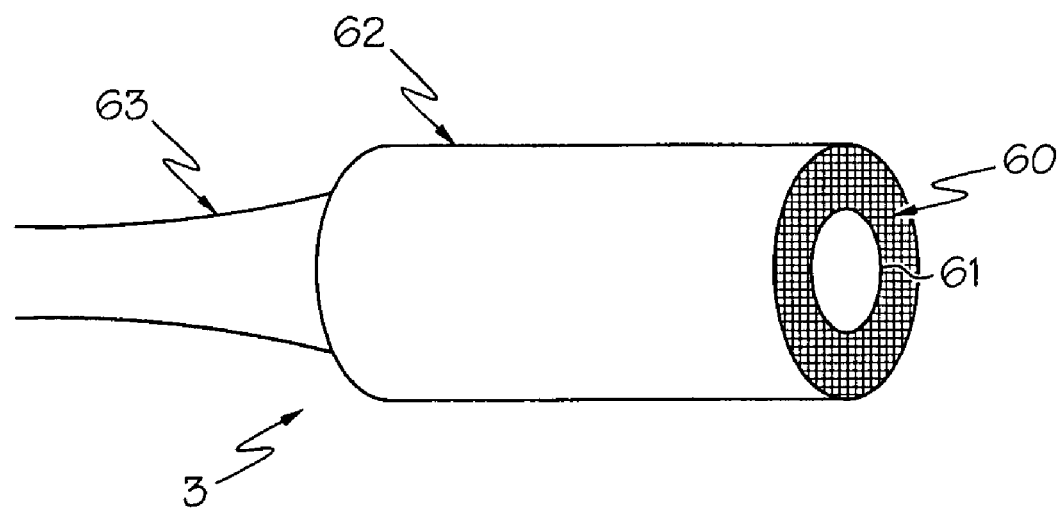
FIG. 8 is a perspective view of an embodiment of a radiation collector.

In another embodiment, as shown in FIG. 8, collector 3 may be configured to be installed coaxially with the scanner assembly 2. Radiation reflected from a scene impinges on the face 60 of the collector 3, which constitutes the receiving aperture. Face 60 is actually made up of the polished ends of a large number of small diameter, multimode collecting fibers 63 which conduct the radiation to the detector assembly 5. Scanner assembly 2 is inserted into a central void 61. The collector 3 is enclosed by a housing 62. The fiber ends making up face 60 may be formed in a plane, or into other geometries to control the pattern of receiving sensitivity. They may be coated with diffusing or other materials to improve their angle of acceptance, to provide wavelength conversion, or wavelength selectivity. In some embodiments, the detector assembly 5 may be configured to form the receiving aperture and mounted in position to receive the reflected radiation directly, without the need for a separate collector 3.

Figure 9:
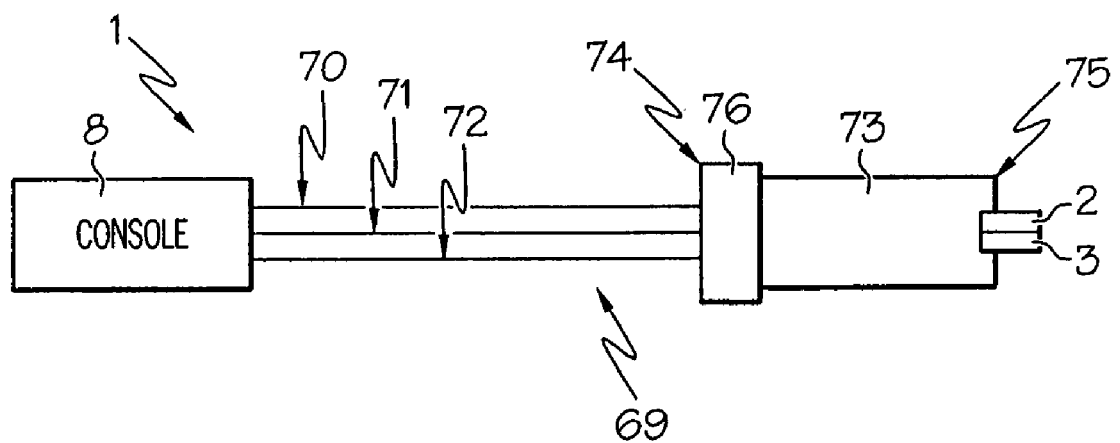
FIG. 9 is a perspective view of an endoscopic configuration of a medical device including a scanner assembly.

FIG. 9 shows diagrammatically various elements previously described as incorporated into an exemplary endoscope 69 for medical use. Endoscope 69 generally includes an elongate, rigid or flexible shaft 73 having a distal end 74 and a proximal end 75 opposite the distal end. There is typically a handle 76 which includes a number of controls, often both mechanical and electrical. In one embodiment, endoscope 69 includes scanning assembly 2 and collector 3. Endoscope 69 may be connected to console 8 by source fibers 70, collection fibers 71, and electrical wiring 72. As used herein, an endoscope refers to an instrument for use in examining, diagnosing and/or treating tissue comprising a patient's body, either percutaneously or through a natural orifice or lumen. As used herein, the term "proximal" refers to a location on the medical device nearer to a user, and the term "distal" refers to a location that is nearer the patient. Typically, the console 8 of the medical device 1 is located outside a patient's body and the distal end of the medical device is insertable into the patient's body. However, other configurations are possible. Furthermore, while an endoscope is referred to, any suitable type of medical device may be employed such as gastroscopes, enteroscopes, sigmoidoscopes, colonoscopes, laryngoscopes, rhinolaryoscopes, bronchoscopes, duodenoscopes, choledochoscopes, nephroscopes, cystoscopes, hysteroscopes, laparoscopes, arthroscopes, etc.

Figure 10:
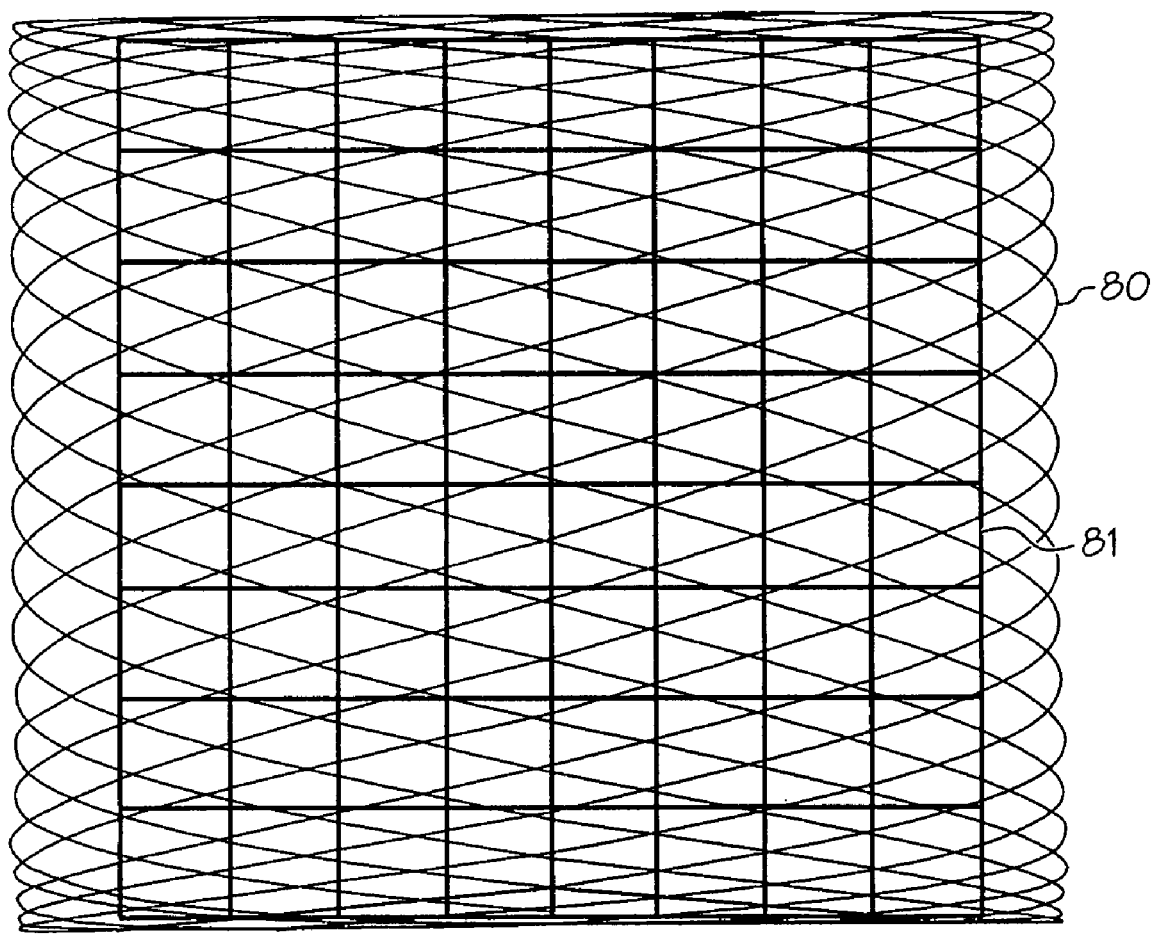
FIG. 10 is an illustration of a bi-sinusoidal scan pattern and a rectangular coordinate pattern plotted together.

Referring now to FIG. 10, as mentioned above, the reflector 27 scans the beam of radiation in a pattern. FIG. 10 shows an idealized bi-resonant or bi-sinusoidal scan pattern. High-speed MEMS reflectors and other resonant reflectors as described herein are configured and driven to execute sinusoidal angular deflections in two orthogonal axes, yielding the classical Lissajous pattern. Most current display devices are configured to address display data in a Cartesian form, for example as row and column, or a particular pixel along a nearly-horizontal scan line. The bi-resonant or Lissajous scan path 80 is shown overlaid with the Cartesian or rectilinear grid 81. In the illustrated instance, the intersections between the vertical and horizontal lines of the Cartesian grid 81 represent display pixel positions while the Lissajous trace 80 represents the actual path taken by the scanned spot. As the actual scan path does not align perfectly with all the rectilinear pixel positions, these image values may be determined through interpolation. In some embodiments, registration of the Lissajous trace 80 to the Cartesian grid 81 is based on a marker that links a reference point in the scan to a point in the rectilinear matrix.

In one embodiment, a user defines a treatment zone, border, or path by identifying the places within the image of the FOV where treatment is to be administered. The user may also select the parameters for the treatment such as the treatment beam wavelength, the power of the beam, and the duration of the exposure. The power of the beam may be modulated by a modulator to achieve the power selected by the user.

Figure 11:
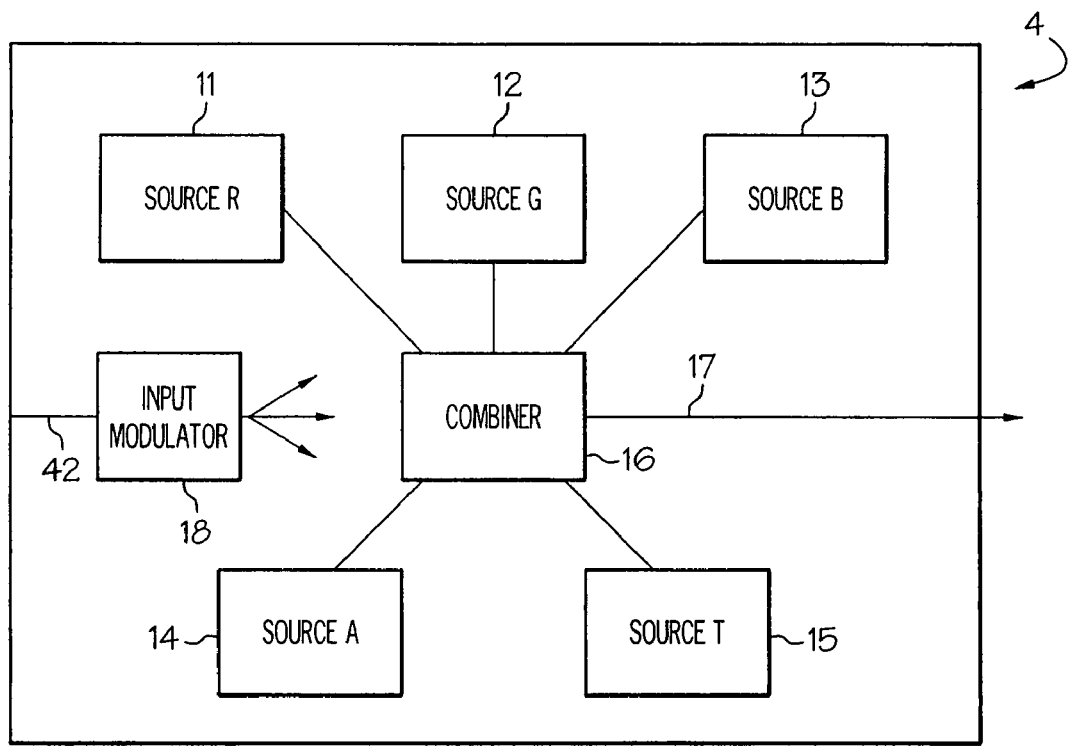
FIG. 11 is a block diagram of the of an embodiment of the source assembly in FIG. 2 including an input modulator.

FIG. 11 illustrates one embodiment of the placement of an input modulator 18 for modulating the power within source assembly 4. Source assembly 4, as illustrated, includes sources 11 through 15, a beam combiner 16, and an input modulator 18. The possible sources 11-15 are described above. Also shown is signal 42 and output beam 17. In one embodiment, modulator 18 may be a control circuit that drives sources 11 through 15 to emit beams of radiation of a specific power. The control circuit may drive the sources by controlling the amount of current in the circuit. For example, if the source is a diode laser a laser driver controller may be used to modulate the power.

Figure 12:
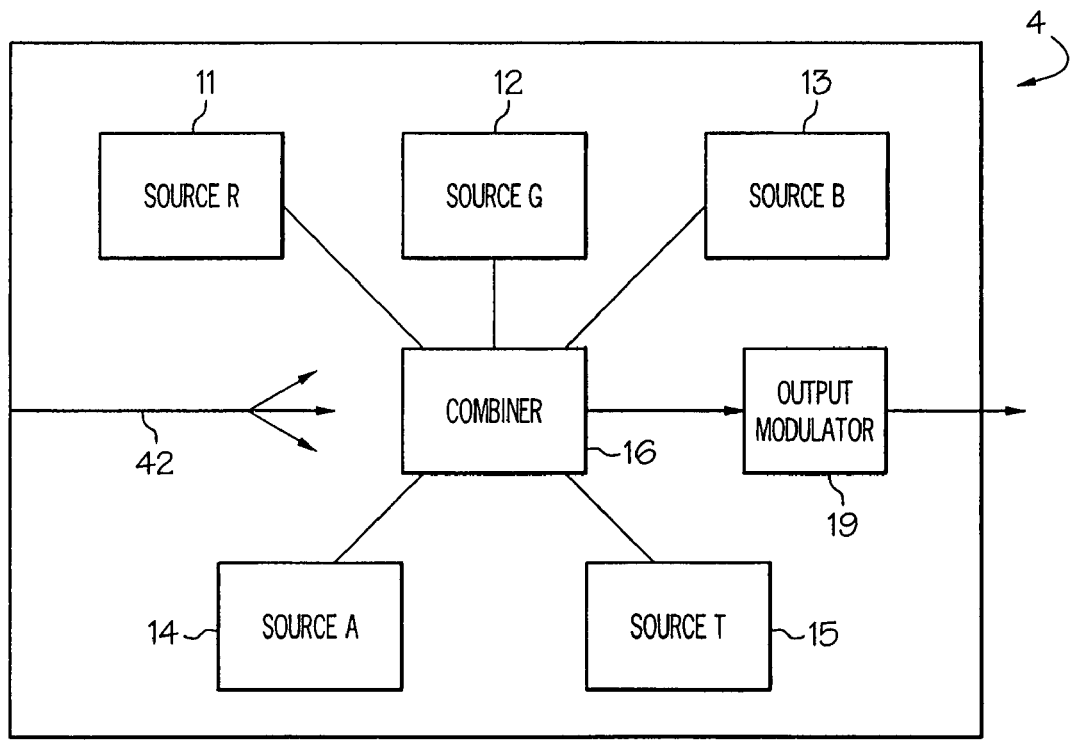
FIG. 12 is a block diagram of the of an embodiment of the source assembly in FIG. 2 including an output modulator

FIG. 12 illustrates another embodiment of the placement of an output modulator 19 for modulating the power that is to exit source assembly 4 as output beam 17. In this embodiment, output modulator 19 modulates the power of the beam after the beam exits beam combiner 16. In one embodiment, beam combiner 16 is not included in source assembly 4 so that output modulator 19 modulates separate beams before the beams exit source assembly 4. Output modulator 19 may be an acoustic-optic modulator Pockels cell, photoelastic modulator, or spatial light modulator that varies the power after the beam(s) of radiation are emitted from sources 11 through 15.

In some embodiments the modulation may be carried out by multiple modulators. In one embodiment, source assembly 4 includes both input modulator 18 and output modulator 19. In another embodiment, several input modulators 18 and output modulators 19 may be included to modulate sources 11 through 15 separately. In another embodiment, the multiple modulators may be positioned between the sources and the beam combiner, such that beams of radiation leaving the source are modulated before entering combiner 16. In yet another embodiment, some sources are modulated with an input modulator 18, while other sources are modulated by an output modulator 19.

In one embodiment, sources 11 through 15 may emit radiation of differing wavelength or beam characteristics (e.g., visible infrared fluorescence excitation, polarized in various ways, circular or elliptical in profile), and as a result each source may require its own compatible modulator. In one embodiment source assembly 4 may have five separate sources, as illustrated in FIGS. 2, 11 and 12. The sources may be a red source 11, a green source 12, a blue source 13, a an aiming source 14, and a therapeutic source 15. In other embodiments, there may be a diagnostic source. Each source may have a different transfer characteristic (i.e., the relation between output power and input control signal is different) so each source may require its own power modulation function. The power modulator for the red source 11 may be programmable to a first function, $f_R(1)$, to keep the red source 11 within a desired exposure range. Likewise, the power modulators for the green source 12 may be programmable to a second function, $f_G(2)$, the blue source 13 to a third function, $f_B(3)$, the therapeutic source 15 to a fourth function, $f_T(4)$, and/or the diagnostic source 14 to a fifth function, $f_D(5)$, to keep each source within the desired exposure range. In another embodiment, a single power modulator may be programmable to evaluate all five functions and determine a sum of the functions to maintain the power of a beam of radiation that is emitted from source assembly 4.

As illustrated in FIG. 1, device 1 has a source assembly 4. Source assembly 4, as shown in FIGS. 11 and 12, includes a modulator for modulating the power of the beam. Device 1 has a controller 6 for controlling the source assembly 4 and the scanner assembly 2 during an imaging procedure, therapeutic procedure, diagnostic procedure, or combinations thereof. The imaging beam, therapeutic beam, diagnostic beam, or combinations thereof are scanned across the FOV and radiation is returned from the surface to collector 2. The scanner assembly deflects the beam from source assembly 4 onto the FOV. The mechanically resonant reflector is capable of deflecting the beam of radiation about two orthogonal scan axes, which results in a first scan direction and a second scan direction. A scan direction can mean a linear direction, or an angular direction. The reflector may be considered to deflect the beam in a linear direction, the magnitude of the scan thus having a length measure, or along angular directions, such as azimuth and elevation, the scan having a measure in angular units. In one embodiment, the resulting scan can be a Lissajous scan.

In one embodiment of the present invention, in any given interval of time the same number of photons are sent from the source assembly 4 when the laser power (i.e. Watts) is held constant. The amount of photons of energy received by a particular sample of tissue will depend on its location within the sinusoidal scanning path. Tissue in the center of the path with be exposed to the beam (i.e. the photons) for a shorter interval of time than tissue at the edge of the FOV where the scanning beam slows down and turns around. To keep the tissues' exposure within a desired range, the power of the beam is modulated using at least one modulator. In one embodiment, the power of the beam is modulated in synchrony with the beam's position in the FOV. The desired range of exposure will determine what maximum exposure level to choose for the particular tissue being imaged, treated, diagnosed, or a combination thereof. Even though the discussion below concerns the position of the beam, the velocity of the beam may also be related to the modulation, and as a result, either the beam's position or the velocity of the beam may be utilized in calculating the function that represents the modulation of the beam.

All the radiation emitted from the scanning beam assembly, whether it is an imaging beam, therapeutic beam, a diagnostic beam, or a combination thereof sweeps across the angular field of view in a sinusoidal manner, as explained above. The sinusoidal is represented by the equation $\theta(t) = A^* \sin(2\pi f_a t)$ where $\theta$ is the angle of deflection of the beam, with 0 being the center; A is the amplitude of the deflection, in angular measure (half the full excursion); $f_a$ is the frequency in the axis of interest, in Hertz or cycles/second; and t is the time.

The field of view may be divided into a number of equal-sized elements, plausibly associated with pixels in the field of view. The size (angular extent) of these is simply $2^*A/N_a$, where $N_a$ is the number of pixels in the axis of interest. To calculate the time spent in each pixel, the time is calculated at which the beam crosses each pixel edge, and then each time is subtracted from the preceding time. Next, the expression is set equal to the expression for $\theta(t)$ as shown above, and the value of $t_n$ is found. The result is $$t_n = \frac{1}{2\pi f_a} * \sin^{-1}\left(\frac{2n}{N_a} - 1\right).$$

Figure 13:
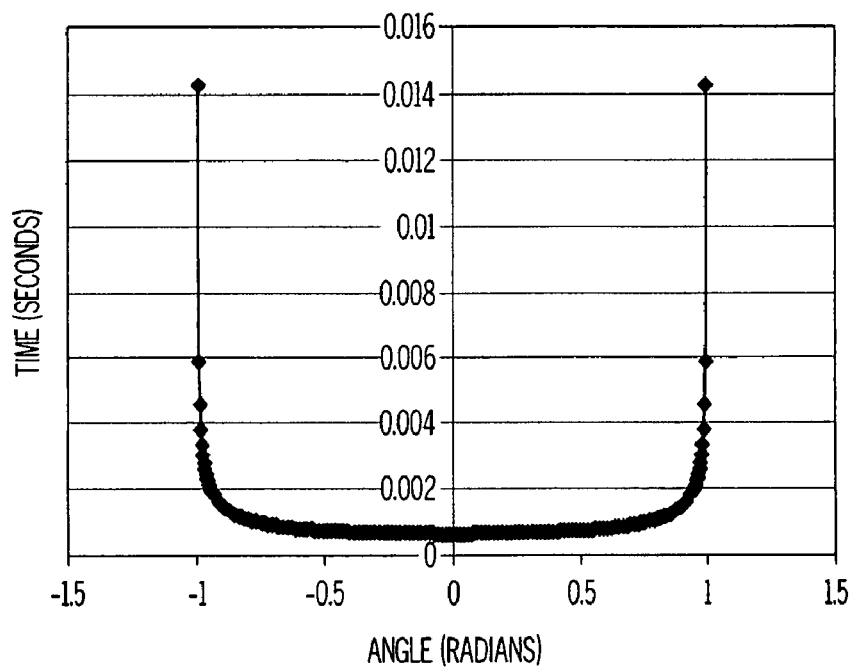
FIG. 13 is a plot of the time spent in angular pixels of the field-of-view with respect to beam position.
Figure 14:
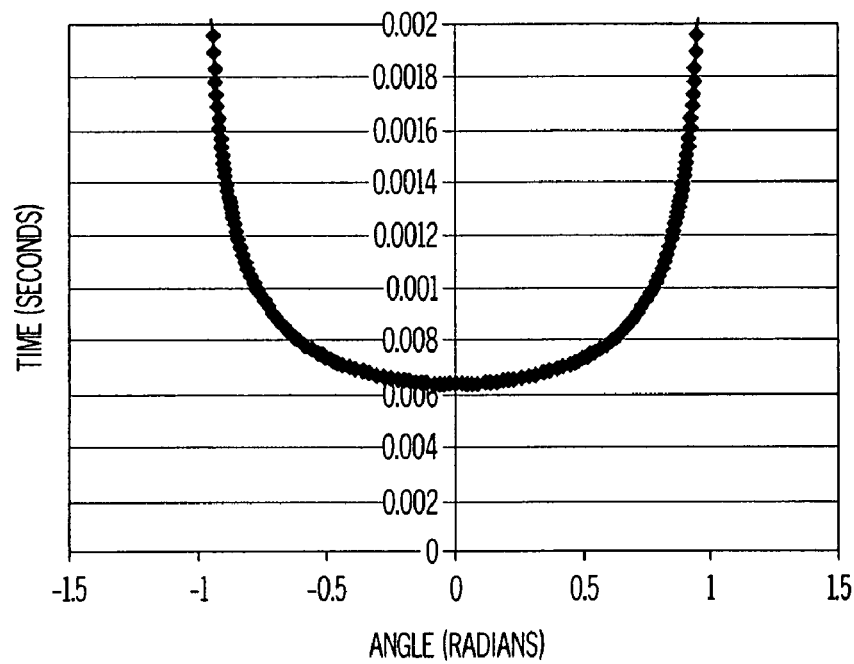
FIG. 14 is an expanded view of the central portion of the plot of FIG. 13.

FIG. 13 shows a plot of this function versus the beam position where $N_a=500$, $A=1$, and $f_a=1$. In the embodiment plotted in FIG. 13, the beam spends about 22 times longer in the pixels at the ends of the scan than it does in the center ones. The central portion of this plot looks rather flat because the plot is scaled to show the extreme end values. FIG. 14 is an expanded plot of the function graphed in FIG. 13 and shows that the curvature is present over the entire scan across the FOV.

The amount of exposure tissue receives from the beam as it passes over the FOV is proportional to the product of the beam's power and the time the beam spends in any region within the FOV. Treatment to be administered to a patient is typically given in terms of a dose to be delivered. The "dose" is a term for the specified amount of energy desired to be delivered to a patient for therapy. To achieve a particular therapeutic effect, the amount of energy delivered in a given area may be specified. The energy may be one watt per one second per square centimeter to cause the desired effect, which is one J/cm². Dose is proportional to the power and the time of exposure.

Figure 15:
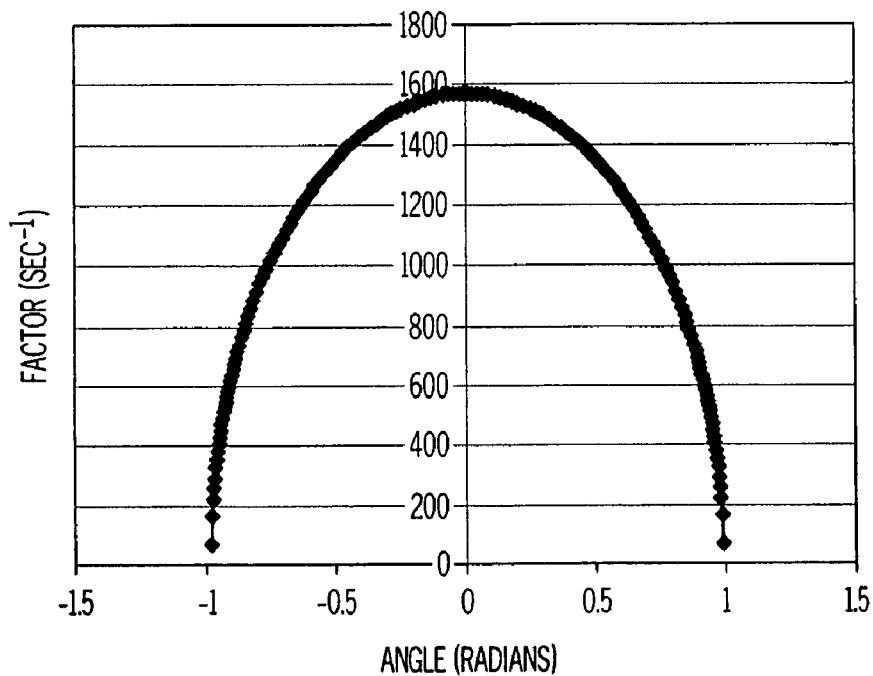
FIG. 15 is a plot of a factor related to the inverse of the time of FIG. 13.

In a system where the time of exposure varies, as shown in FIG. 13, the power can be varied, or modulated to achieve the specified dose. Then the power may be modulated as the inverse of the time spent to keep the exposure within the desired range. FIG. 15 shows one embodiment of a plot of varying power of a beam of radiation as a function of the inverse of the time as the beam scans the FOV. Modulators 18 and 19 may need to vary the power of sources 11 through 15 to achieve a dose distribution that may allow several watts in the smaller increment of time spent in the center of the FOV while allowing only milliwatts in the larger increment of time spent at the edge of the FOV. In one embodiment the edge of the FOV has an allowable power of about 20 milliwatts.

While the power modulation function may be the inverse to the time the beam spends in a region of the FOV, those skilled in the art will recognize as described herein that more complex functions are also feasible where, in addition to the time spent, the type of source used, the function may take into consideration characteristics of the tissue that may warrant an increase or decrease in the power (e.g., the geometry of the tissue and the way the geometry changes the amount of the radiation reflected therefrom, or multiple tissue types that may make up one FOV, etc.). For example, as the beam scans away from the centerline of the scan pattern the shape of the illuminated spot changes. If the spot was a circle to begin with, as an example, it becomes more elliptical and its area increases as the beam scans away from the centerline. This increase in area and change in shape may be an additional factor in developing the power modulation schedule. Another factor that may be considered is the optical properties of the tissue being treated.

When treating or diagnosing tissue with a therapeutic or diagnostic beam the spot size on the tissue exposed to the beam may vary in location within the FOV, according to the geometry of the target. There may be multiple regions of varying size within the FOV which need to be treated or diagnosed. As mentioned above, the spot size may also vary according to the geometry of the target. The above analysis was performed in angular space and the deflection angle was calculated as a function of time, where the FOV was divided into constant angular elements. If the range to the target is constant, then the distance occupied by each angular element is also constant, that distance being given by $$d = r*\theta$$

where d is the distance from one edge of the pixel to the next (its length, or width), r is the range from the scanning device to the target, in consistent units, and θ is the angular extent of the pixel in radians.

The range is constant if the target surface is cylindrical (for a one-axis scanner) or spherical (for a two axis scanner) and in both cases centered on the scanner. While this geometry may be approximately true for some scenes, more often the target is approximately planar, or can be treated as such over a limited extent. For this case, with the target plane normal to the centerline of the field of view, further adjustments may be desirable to achieve a constant dose.

Optical properties of many materials of interest exhibit directional behavior. In particular, a scattering anisotropy parameter "g," the mean cosine of the scattering angle, is often used to describe how the angle of incidence of radiation affects the reflected and absorbed radiation. In many cases, light arriving at a tissue surface at an angle is largely reflected away from the tissue rather than being absorbed. As the beam scans away from the centerline, this factor comes into play. As the beam scans away from the centerline, it is increasingly oblique to the surface and the beam shape is distorted. For example, if the scan spot is a circle to start with, it becomes elliptical, and its area increases. The dose in a given area decreases as the beam's power is distributed over larger areas. Also, as the beam scans away from the centerline, the range is increasing, and the overall size of the illuminated spot increases, which again decreases the dose.

Figure 16:
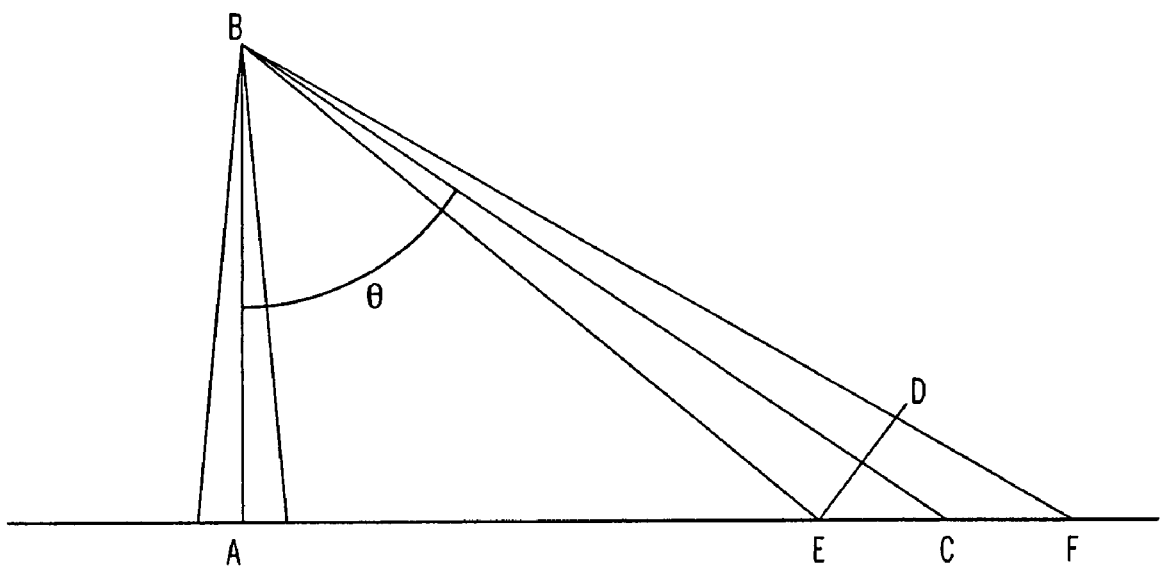
FIG. 16 is a schematic illustration of the relationship between beam position and illuminated spot size.

The function for modulating the power of the beam as it scans the FOV may be modified to account for the distortion in the beam's shape and the increase in spot size as the beam scans away from the centerline. FIG. 16 illustrates a beam of radiation (whether it be imaging, therapeutic, or a diagnosing beam) that originates from a reflector 27 positioned at B. The central beam to the target impinges at A, and a beam at angle θ impinges at C to illuminate a spot. DE is perpendicular to beam impinging at C. EF is the extent of the beam at C. The range to the target at angle θ is BC. Since AB/BC is cos(θ), BC is AB/cos(θ). The size of an object is the range multiplied by its angular extent, so the spot size in both the horizontal direction shown and the direction out of the plane varies as 1/cos(θ).

Furthermore, there is a geometric distortion of the spot. Because of the beam's inclination to the target, the spot is elongated from a circle of diameter DE to an ellipse of major axis EF. Triangles ABC and DEF are similar. BC varies as 1/cos(θ) and so does EF. Therefore, the area covered by the spot must vary as $(1/\cos(\theta))^3$, the width varying as 1/cos(θ) and the length as 1/cos(θ) squared. So to achieve a specified dose, the power, as a function of angle, must be further multiplied by $(1/\cos(\theta))^3$.

Figure 17:
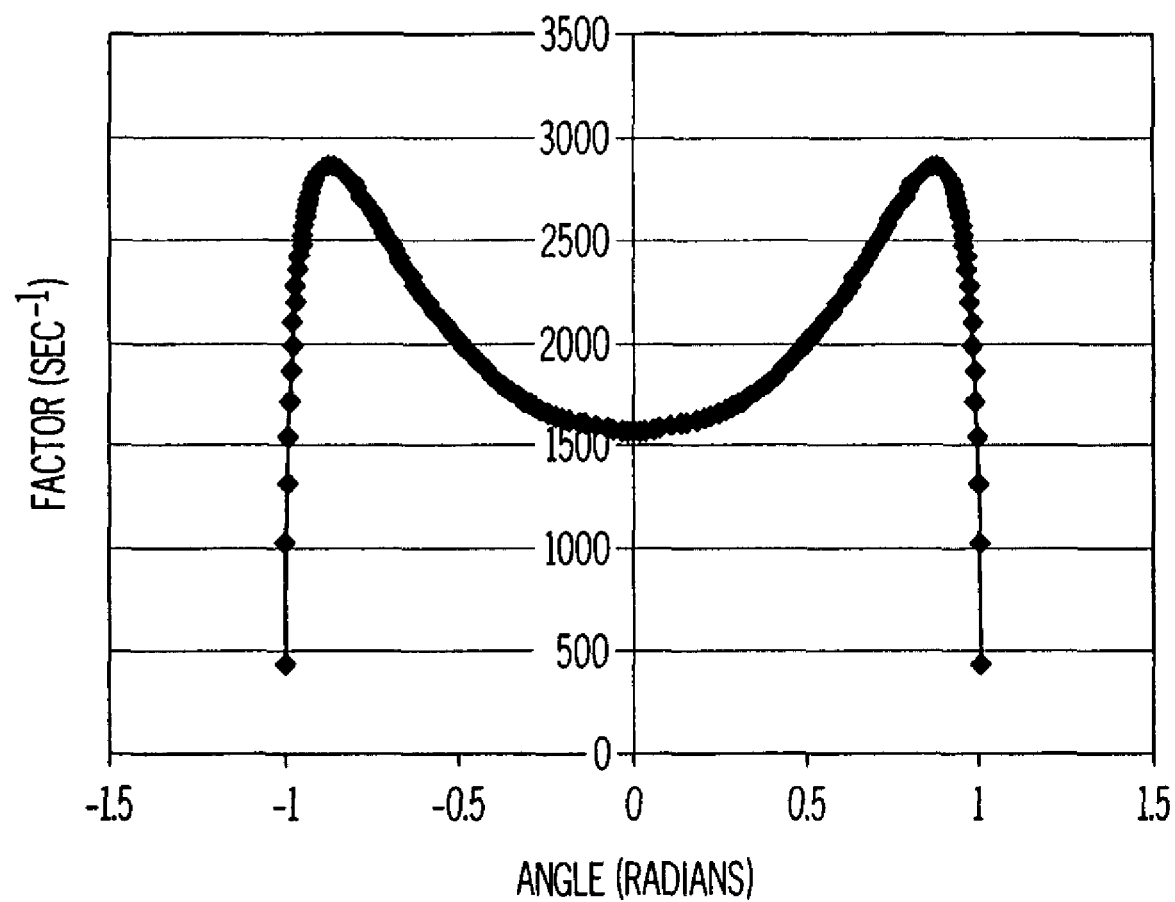
FIG. 17 is a plot of the modulation of the power of as a more complex function of beam position.

To achieve a constant dose across the FOV the power is modulated, including varying the power with respect to the beam's velocity and the spot size as just explained. FIG. 17 is a plot of the inverse of the time spent in a region of the FOV multiplied by $(1/\cos(\theta))^3$. The resulting function illustrated by FIG. 17 is $[\arcsin(\text{angle})*\cos^3(\text{angle})]^{-1}$. As opposed to when the range is held constant, FIG. 17 shows that the rapid growth in the beam area with angle initially calls for increasing power as the beam moves away from the centerline. Yet, at the edges of the FOV, the slow beam velocity overcomes this trend and allows the power to be reduced. It should be understood that the analysis above may be performed for other scanning parameters, and may lead to other shapes for the characteristic relationships.

The dynamic range of the power of the imaging beam contains the various power levels at which the assembly can operate as the beam scans across the FOV. If the power level falls below some lower limit the imaging beam may not have enough power to be detectable upon reflectance from the surface of the FOV. If the power level rises above some maximum allowed value the tissue may be damaged or the collectors or detectors may be overpowered by the exposure to the beam of radiation. To avoid tissue damage or overpowering the collectors or detectors if the power exceeds the maximum allowable power, the scanning beam assembly of some embodiments may turn the source(s) assembly off, for all or a portion of the FOV, or for some fraction of the time that the therapeutic beam is emitted.

In some embodiments the scanning beam assembly is scanning beam imager where the power is modulated only for imaging sources. In other embodiments the scanning beam assembly is a scanning beam treatment system where the power is modulated for the therapeutic sources. In another embodiment the scanning beam assembly is a scanning beam diagnostic system where the power is modulated for the diagnostic source. Additionally, other embodiments, may be any combination of the above imaging, treating, or diagnosing scanning beam systems. If the scanning beam assembly is a scanning beam treatment or diagnostic system without the imaging system, a tracer beam may be needed to sweep out the same area of the treatment beam. The tracer beam may be visible to the imaging system.

A number of detailed embodiments have been described. Nevertheless, it will be understood that various modifications may be made. Accordingly, other embodiments are within the scope of the following claims.

What is claimed is:

1. An assembly comprising:
    a radiation source to generate a beam of radiation;
    a modulator for modulating the power of the beam of radiation as a function of the position of the beam within a field-of-view to maintain a desired exposure level as the beam scans the field-of-view; and
    a reflector oscillating in a sinusoidal manner to direct the beam of radiation onto a field-of-view as a bi-sinusoidal scan of a target surface within the field-of-view;
    wherein the target surface is assumed to be approximately planar and the modulator continuously modulates the power of the beam according to the function $[\arcsin(\text{angle})*\cos^3(\text{angle})]^{-1}$ to account for a geometric distortion of the spot size of the beam during the bi-sinusoidal scan.

2. The assembly of claim 1 wherein the reflector is at least part of a medical instrument.

3. The assembly of claim 1 wherein the modulator is at least one of a laser driver, an acoustic-optic modulator a Pockels cell, a photoelastic modulator, and a spatial light modulator.

4. The assembly of claim 1 wherein the desired exposure level is a constant dose of a radiation during the bi-sinusoidal scan.

5. The assembly of claim 4 wherein the modulator modulates the radiation source that emits a therapeutic beam at the constant dose.

6. The assembly of claim 5 wherein the radiation further includes an imaging beam, diagnostic beam, or a combination thereof.

7. The assembly of claim 1 wherein the modulator is an input modulator, an output modulator, or a combination thereof.

8. The assembly of claim 7 further comprising a beam combiner coupled to the input modulator, the output modulator, or the combination thereof.

9. An assembly comprising:
   a radiation source to generate a beam of radiation, the radiation source including at least one of a therapeutic beam, and a diagnostic beam;
   a modulator for modulating the power of the beam of radiation as a function of the position of the beam within a field-of-view to maintain a desired-power of the beam of radiation as the beam scans the field-of-view; and
   a reflector oscillating in a sinusoidal manner to direct the beam of radiation onto a field-of-view as a bi-sinusoidal scan of a target surface within the field-of-view, wherein the reflector is at least part of a medical instrument;
   wherein the target surface is assumed to be approximately planar and the modulator continuously modulates the power of the beam according to the function $[\text{arcsine}(\text{angle})*\cos^3(\text{angle})]^{-1}$ to account for a geometric distortion of the spot size of the beam during the bi-sinusoidal scan.

10. The assembly of claim 9 wherein the modulator is at least one of a laser driver, an acoustic-optic modulator, a Pockels cell, a photoelastic modulator, and a spatial light modulator.

11. The assembly of claim 9 wherein the radiation further includes an imaging beam, a therapeutic beam, a diagnostic beam, or a combination thereof.

12. The assembly of claim 11 further comprising a beam combiner coupled to the input modulator, the output modulator, or the combination thereof.

13. The assembly of claim 12 wherein the modulator is an input modulator, an output modulator, or a combination thereof.

14. The assembly of claim 13 wherein only the imaging beam is modulated by the modulator.

15. The assembly of claim 13 wherein only the diagnostic beam is modulated by the modulator.

16. The assembly of claim 13 wherein only the therapeutic beam is modulated by the modulator.

* * * * *